United States Patent [19]

Egly et al.

[11] Patent Number: 5,780,679
[45] Date of Patent: Jul. 14, 1998

[54] SEPARATION OF (METH)ACRYLIC ACID FROM THE REACTION GAS MIXTURE FORMED IN THE CATALYTIC GAS PHASE OXIDATION OF $C_3/C_4$ COMPOUNDS

[75] Inventors: Horst Egly, Böhl-Iggelheim; Volker Diehl, Ellerstadt; Klaus Jörg, Limburgerhof, all of Germany

[73] Assignee: BASF Aktiengesellschaft, Ludwigshafen, Germany

[21] Appl. No.: 541,425

[22] Filed: Oct. 10, 1995

[30] Foreign Application Priority Data

Oct. 11, 1994 [DE] Germany ............... 44 36 243.9

[51] Int. Cl.$^6$ ................................................. C07C 51/42
[52] U.S. Cl. ................................................. 562/600
[58] Field of Search ................................................. 562/600

[56] References Cited

U.S. PATENT DOCUMENTS

| | | | |
|---|---|---|---|
| 3,736,355 | 5/1973 | Croci et al. | 260/533 N |
| 3,868,417 | 2/1975 | Duembgen et al. | 260/526 N |
| 3,932,500 | 1/1976 | Duembgen et al. | 260/526 N |
| 4,110,370 | 8/1978 | Engelbach et al. | 260/530 N |
| 4,156,633 | 5/1979 | Horlenko et al. | 203/93 |
| 4,925,981 | 5/1990 | Shimizu et al. | 562/600 |
| 5,198,576 | 3/1993 | Etzkorn et al. | 562/532 |
| 5,364,825 | 11/1994 | Neumann et al. | 502/311 |
| 5,426,221 | 6/1995 | Willersinn et al. | 562/600 |
| 5,449,821 | 9/1995 | Neumann et al. | 562/546 |

FOREIGN PATENT DOCUMENTS

| | | |
|---|---|---|
| 02 53 409 | 1/1988 | European Pat. Off. . |
| 19 62 431 | 6/1970 | Germany . |
| 21 36 396 | 2/1973 | Germany . |
| 22 41 714 | 3/1974 | Germany . |
| 24 49 780 | 4/1976 | Germany . |
| 25 44 930 | 4/1976 | Germany . |
| 42 20 859 | 1/1994 | Germany . |
| 43 08 087 | 9/1994 | Germany . |
| 44 05 059 | 8/1995 | Germany . |

*Primary Examiner*—Gary Geist
*Assistant Examiner*—Rosalynd Keys
*Attorney, Agent, or Firm*—Oblon, Spivak, McClelland, Maier & Neustadt, P.C.

[57] ABSTRACT

A process for the separation of (meth)acrylic acid from the reaction gas mixture formed in the catalytic gas phase oxidation by countercurrent absorption using a high-boiling inert hydrophobic organic liquid, in which the reaction gas mixture is passed through an absorption column countercurrently to the descending high-boiling inert hydrophobic organic liquid and (meth)acrylic acid is subsequently fractionally separated from the liquid effluent leaving the absorption column and containing (meth)acrylic acid, wherein a rectifying process is superimposed on the absorption process occurring naturally in the absorption column by removing a quantity of energy from the absorption column which exceeds its natural energy loss resulting from contact with the ambient atmosphere.

11 Claims, No Drawings

SEPARATION OF (METH)ACRYLIC ACID FROM THE REACTION GAS MIXTURE FORMED IN THE CATALYTIC GAS PHASE OXIDATION OF $C_3/C_4$ COMPOUNDS

The present invention relates, in particular, to a novel process for the separation of acrylic acid from the reaction gas mixture formed in the catalytic gas phase oxidation of propylene and/or acrolein by counter-current absorption using a high-boiling inert hydrophobic organic liquid, in which the reaction gas mixture is passed through an absorption column countercurrently to the descending high-boiling inert hydrophobic organic liquid and acrylic acid is subsequently fractionally separated from the liquid effluent leaving the absorption column and containing acrylic acid.

Due to its very reactive monoethylenically unsaturated bond and its acid function acrylic acid forms a valuable monomer for the preparation of polymers, eg for aqueous polymer dispersions suitable for use as adhesives. The same applies to methacrylic acid.

Acrylic acid is available, inter alia, by gas phase oxidation of propylene and/or acrolein with oxygen or gases containing oxygen in the presence of catalysts (eg multimetal oxides containing the elements molybdenum and vanadium in oxidic form) at elevated temperature and also due to the high heat of reaction preferably with dilution of the reactants with inert gases such as $N_2$, $CO_2$ and/or hydrocarbons and/or steam. In this process there is obtained however not pure acrylic acid, but a reaction gas mixture which contains, as secondary components apart from acrylic acid, substantially unconverted acrolein and/or propylene, steam (also formed as reaction product), carbon oxides, inert diluent gas (eg nitrogen), lower aldehydes such as formaldehyde, maleic anhydride and, in particular, acetic acid (cf eg EP-A 253,409 and DE-A 1,962,431), from which the acrylic acid must be subsequently separated. The isolation of methacrylic acid is similarly possible starting from $C_4$ compounds and is encumbered with similar problems.

DE-PS 2,136,396 and DE-A 4,308,087 disclose that it is possible to separate acrylic acid from the reaction gas mixture formed in the catalytic gas phase oxidation of propylene and/or acrolein by countercurrent absorption using a high-boiling inert hydrophobic organic liquid.

The process is essentially carried out by passing the reaction mixture through a conventional absorption column countercurrently to the descending liquid absorbent, then, in a desorption column, substantially removing the readily volatile secondary components from the liquid effluent leaving the absorption column and substantially composed of acrylic acid, the absorbent, and secondary components by stripping, and subsequently rectifying the liquid effluent leaving the desorption column for the purpose of separating substantially pure acrylic acid and also less readily volatile secondary components.

A disadvantage of this method is that the desorber off gas (the stripping gas used) entrains in normal operation of the desorption column at least one third of the acrylic acid present in the liquid effluent leaving the absorption column and passed to the desorption column, for which reason the desorber off gas must be recycled to the absorption column (cf section 1 on page 7 of DE-A 2,136,396). In this way the prior process circulates a not inconsiderable amount of acrylic acid to be separated with no separating effect, which impairs the economical value of the method used in the prior art to a considerable extent.

It is thus a particular object of the present invention to provide a process for the continuous separation of acrylic acid from the reaction gas mixture formed in the catalytic gas phase oxidation of propylene and/or acrolein by effecting countercurrent absorption using a high-boiling inert hydrophobic organic liquid, which does not suffer from the drawbacks of the prior processes.

Simply omitting the desorption step provides no solution to the present problem, since the direct introduction of the liquid effluent from a conventional absorption column into a rectifying column, would, particularly due to the fact that such a liquid effluent still contains quantities of secondary components (low-boilers) which boil, under standard pressure conditions, at temperatures which are below the boiling point of acrylic acid but are not very different from acrylic acid (liquid at 20° C. and standard pressure (1 atm), exceed the separating capabilities of conventional rectifying columns (for example, high base temperatures would be necessary in order to maintain the required temperatures for the number of separating stages and this would be inacceptable due to the high polymerization proneness of acrylic acid).

In order to achieve the desired object, we have found a process for the continuous separation of acrylic acid from the reaction gas mixture formed in the catalytic gas phase oxidation of propylene and/or acrolein by countercurrent absorption using a high-boiling inert hydrophobic organic liquid, in which the reaction gas mixture is passed through an absorption column countercurrently to the descending high-boiling inert hydrophobic organic liquid and acrylic acid is subsequently fractionally separated from the liquid effluent leaving the absorption column and containing acrylic acid, wherein a rectifying prozess is superimposed on the absorption process occurring naturally in the absorption column by removing a quantity of energy from the absorption column which exceeds its natural energy loss resulting from contact with the ambient atmosphere.

Possible embodiments include both indirect cooling of the absorption column by means of cooled heat-transfer means (eg heat-transfer means comprising jackets, coils, tube bundles, double pipes, spirals, or panels) and/or direct cooling.

A particularly advantageous variant of an energy sink consist in withdrawing a portion of the descending liquid phase at a point along the absorption column, cooling it and subsequently recycling the cooled fluid to the absorption column.

Suitable absorption columns are all of the commonly used types, ie the absorption is column can be, eg, a valve tray column, a bubble-cap tray column, a column filled with a loose, irregular, packing, or a column filled with compact packs. Compact-packed columns are preferred, packed columns containing regular (well-ordered) compact-packs being particularly advantageous. Packed columns containing regular packs are known to the person skilled in the art and are described in, eg, Chem.-Ing. Tech. 58 (1986) No. 1, pp 19–31 and Technische Rundschau Sulzer 2/1979 pp 49 et seq published by Gebrüder Sulzer Aktiengesellshaft, Winterthur, Switzerland. According to the invention, the use of sheet-metal or plate packs has been found to be advantageous. The use of Mellapak® column packs sold by Sulzer AG, eg those of type 250 Y or type 125 Y, is particularly advantageous. Regular packs are particularly characterized by low pressure losses and guarantee small residence times, which is advantageous in view of the high polymerization proneness of acrylic acid.

The absorption column advantageously contains 5 to 20 theoretical separating stages, depending on the concentration, in the gas mixture to be rectified, of by-products boiling at a temperature below the boiling point of acrylic acid under standard pressure conditions and liquid at 20° C. under standard pressure conditions (low-boilers), particularly acetic acid and water. The reaction gas mixture withdrawn from the gas phase oxidation usually contains 1 to 10 wt % of low-boilers, based on the acrylic acid present therein.

The absorbent is usually introduced at the top of the absorption column, whilst the gaseous reaction mixture normally enters at the bottom of the absorption column. If the energy sink required by the present invention is realized by withdrawing a portion of the descending liquid phase at a point along the absorption column, cooling this portion and subsequently recycling the cooled portion to the absorption column, this withdrawal is carried out advantageously at a point near the halfway mark of the absorption column, and recycling is usually carried out at a point slightly above the point of withdrawal.

Suitable high-boiling inert hydrophobic organic liquid absorbents are all those whose boiling temperature under standard pressure conditions is above the boiling temperature of acrylic acid and which to an extent of at least 70 wt % consist of molecules which contain no outwardly effective polar groups and thus, for example, are not capable of forming hydrogen bridges.

Thus suitable liquid absorbents are particularly all those recommended in DE-A 2,136,396 and DE-A 4,308,087. These are substantially liquids whose boiling point under standard pressure conditions is above 160° C. The following may be mentioned by way of example only: middle oil fractions from the distillation of paraffin, diphenylether, diphenyl, or mixtures of the aforementioned liquids such as a mixture of 70 to 75 wt % of diphenylether and 25 to 30 wt % of diphenyl. The use of a mixture comprising a blend of 70 to 75 wt % of diphenylether and 25 to 30 wt % of diphenyl, and also, based on this mixture, 0.1 to 25 wt % of o-dimethyl phthalate, is particularly advantageous.

In a manner suitable for these liquid absorbents the reaction gas mixture leaving the oxidation reactor and typically having a temperature of from 200° to 350° C. is advantageously cooled to a temperature of from 190° to 230° C. and preferably of from 200° to 210° C. prior to entering the absorption column. This cooling is preferably effected by indirect heat exchange, for example in order to avoid formation of an aerosol as frequently occurs in the case of direct cooling with a liquid.

This indirect heat exchange is usually carried out in a shell-and-tube heat exchanger. The coolant used can be for example boiling water (under pressures of up to 12 bar) or alternatively one of the possible liquid absorbents. It is important to ensure that when executing this cooling the temperature of the reaction gas mixture does not fall below its dew point. If the reaction gas mixture leaving the oxidation reactor already has a suitable absorption temperature, the indirect cooling step is of course not necessary.

The introduction of the absorbent at the top of the column normally takes place in liquid form distributed over the entire cross-section of the packed column (sprinkling technique), the liquid absorbent usually having a temperature of from 50° to 100° C. and preferably from 50° to 70° C.

The absorption column is usually operated under slightly elevated pressure. The operating pressure is preferably between 1 and 2 bar.

If the energy sink required by the present invention is realized by withdrawing a portion of the descending liquid phase at a point along the absorption column, cooling this portion and subsequently recycling the cooled liquid to the absorption column, the wall of the absorption column is itself normally in direct contact with the atmosphere surrounding it, which usually has room temperature. Possible wall materials are, theoretically, all suitable materials, such as ceramics or glass, but high-grade steel is preferred. As regards the selection of the wall material, properties such as corrosion resistance and mechanical resistance are of prime importance. Typical high-grade steel wall thicknesses are 4 to 20 mm.

The energy sink, operating pressure, and pressure loss of the column and the type of absorbent used are advantageously selected such that the bottom theoretical separating stage has a temperature of from 110° to 125° C. and preferably from 115° to 120° C. and the temperature at the top theoretical separating stage is 5° to 15° C., preferably 10° C., above the input temperature of the absorbent. This may be effected, for example, by withdrawing only a relatively small amount of liquid and recycling this in a highly cooled state, or by withdrawing a relatively large amount of liquid and cooling this only moderately. Such withdrawal of the descending liquid can be realized, for example, by the use of a covered flue structure, in which the flue, due to its cover, allows only the ascending steam/gas mixture to pass through it, whilst the flue base onto which the descending liquid runs has overflow tubes (preferably four overflow tubes disposed symmetrically around the flue located at the center ). The liquid which has accumulated up to the overflow level can be withdrawn from the flue base in known manner.

The bottoms of the absorption column contain, in the process of the invention, the low-boilers, particularly acetic acid, impoverished extremely efficiently (usually containing only 0.1 to 1 wt %, based on the acrylic acid present, ie approximately one tenth of the original content), which makes it possible to work up the bottoms directly by fractional distillation in known manner, without having to go through the intermediate step of desorption, and to separate, during this phase, an acrylic acid having a purity of at least 99.7 wt %.

The process of the invention is preferably carried out continuously. The weight of high-boiling hydrophobic inert organic liquid fed to the top of the absorption column is usually four to eight times greater than the weight of acrylic acid fed in over an identical period via the reaction gas mixture to be purified.

The high-boiling organic liquid formed when executing the fractional separation of acrylic acid from the bottoms of the absorption column can, when the process of the invention is carried out continuously, be directly reused as absorbent and recycled to the top of the absorption column. In order to increase the operating times of the plant it may be recommendable to tap off a partial stream of this high-boiling organic liquid and to return it only after separation of virtually non-volatile impurities contained therein in higher concentrations.

In this embodiment of the process of the invention the polymerization inhibitor required, of course, in all process steps (except when cooling the reaction gas mixture to the absorption temperature), eg, phenothiazine, is advantageously added to the whole system at the top of the rectifying column used for separating the acrylic acid.

Another recommendation is to use a column containing regular packs for the fractional separation of acrylic acid from the bottoms of the absorption column and to withdraw acrylic acid through a side flue.

It is particularly advantageous to apply the process of the invention to reaction gas mixtures formed in the gas-phase catalyzed oxidative preparation of acrylic acid, such as are obtained, eg. by the process described in DE-A 4,220,859.

Theoretically, the steam/gas mixture emerging at the top of the absorption column in the process of the invention can be removed from the system.

Advantageously, however, a secondary column (which may, theoretically, be of the same type as is employed for the main column) will be mounted on the main column described above, where passage from one column to the other is possible only for the ascending steam/gas mixture, in which secondary column the ascending steam/gas mixture is caused to pass countercurrently to cold water fed to the top of said secondary column. The main purpose of the secondary column consists in condensing the components of the steam/gas mixture ascending in the secondary column and condensable at the temperature of the cold water fed thereto so that at the top of this column a mixture is removed which contains virtually only the inert diluent gases such as $N_2$, etc co-used when executing the gas-phase catalyzed oxidative preparation of acrylic acid and also portions of the reaction gas mixture formed when the gas phase oxidation is effected by, eg. total combustion to produce carbon oxides.

Thus, theoretically, there is no need for the secondary column to contain more than a single theoretical condensing step. However, the secondary column is preferably designed so as to include 2 to 4 theoretical condensing steps. The descending liquid accumulating at the bottom of the secondary column usually separates into a predominantly aqueous phase, which contains, in particular, considerable amounts of the mostly highly water-soluble by-products such as acetic acid boiling at a temperature below the boiling point of acrylic acid and into an organic phase comprising mainly absorbent and usually of greater specific gravity. When the process is carried out continuously, part of the aqueous phase and, with this, the low-boilers present therein, are advantageously separated and removed, whilst the remaining residual amount is cooled and recycled to the secondary column at the top of the secondary column instead of the fresh water introduced at the commencement of the process. Similarly, the cold water is cooled to the requisite temperature, ie usually to a temperature of from 5° to 30° C. and preferably from 5° to 25° C. and the aqueous phase removed following separation is withdrawn at such a rate that the amount of water present therein corresponds to the amount of steam removed by condensation, in the secondary column, from the steam/gas mixture ascending the main column. The organic phase coming from the base of the secondary column is normally recycled to the main column, preferably at the top thereof.

In the secondary column, condensation, absorption, and phase-deterioration processes overlap. Preferably the secondary column used is likewise a packed column containing regular packs.

The cold water is fed to the top of the secondary column at such a rate that it produces the desired condensing effect without causing flooding of the column. Thus this rate naturally depends on the input temperature used.

In practice the superimposed arrangement of main column and secondary column will advantageously be realized by the use of a single column in which a lower section (corresponding to the main column ) is separated from an upper section (corresponding to the secondary column) in such a manner that only the ascending steam/gas mixture can pass through to said upper section. This can be realized, eg. by the use of a flue structure having a covered flue and an impassable flue base. Thus the flue base serves as a collecting plate for the descending liquid phase coming from the upper section of the column, which phase separates, on this collecting plate, as described above, into a predominantly organic phase and a predominantly aqueous phase.

The object of the invention is achieved in a particularly preferred manner by providing a process for the separation of acrylic acid from the reaction gas mixture formed in the catalytic gas phase oxidation of propene and/or acrolein by countercurrent absorption using a high-boiling inert hydrophobic organic liquid, in which the reaction gas mixture is passed through an absorption column countercurrently to the descending high-boiling inert hydrophobic organic liquid and acrylic acid is subsequently fractionally separated from the liquid effluent leaving the absorption column and containing acrylic acid wherein the reaction gas mixture exhibiting the necessary temperature is fed in below the bottom pack in a packed column equipped substantially throughout with regular packs and divided into two sections which are separated from each other by a junction which allows only the passage of the ascending steam/gas mixture, where the ascending reaction gas mixture fed to the lower section below the bottom pack (feed point 1) is passed countercurrently to the high-boiling hydrophobic organic absorbent fed in at a point above the top pack of the lower section (feed point 2), distributed over the entire cross-section of the column, and a portion of the descending liquid phase is withdrawn at a point along this section of the column and is cooled and returned to the packed column at a point between this point of withdrawal (point of withdrawal 1 ) and feed point 2 after having been cooled, the steam/gas mixture traveling up through said junction is passed passes up through the upper section of the packed column countercurrently to a stream of cold water which is fed to the column at a point above the top pack (feed point 3), distributed over the entire cross-section of the column, the junction being formed as a collecting point for the descending liquid phase from the upper section of the column, which liquid phase separates at this collecting point into a predominantly organic phase and a predominantly aqueous phase, and the organic phase accumulating at the collecting point is withdrawn from the collecting plate and returned to the lower section of the column, and the aqueous phase accumulating at the collecting point is also withdrawn (point of withdrawal 2), a portion of the withdrawn aqueous phase being separated off and removed such that the weight of water present in this portion is equal to the weight of steam removed by condensation from the steam/gas mixture ascending through said dividing junction, and the remainder of the withdrawn aqueous phase is cooled and recycled to the feed point 3 in the upper section of the column, whilst the gas phase which has not been liquefied by the cold water is withdrawn at the top of the column and removed and the liquid at the base of the column, mainly consisting of acrylic acid and the high-boiling hydrophobic organic absorbent, is transferred directly to a rectifying column where acrylic acid is fractionally separated from said bottoms in known manner.

Preferably the said rectifying column has more than 20 theoretical separating stages and is operated under reduced pressure. It is particularly advantageous to carry out the process at a head pressure of less than 100 mbar. It is particularly advantageous to effect the evaporation necessary when executing said rectification by using a falling-film evaporator and thus carrying out the evaporating process under careful conditions.

Of course, the process of the invention can also be used for the separation of methacrylic acid from the reaction gas mixture coming from the catalytic gas phase oxidation Of $C_4$ or masked $C_4$ starting compounds (eg butene, tert-butenol, ethers of tert-butanol, methacrolein etc, cf eg DEA 4,405,059) in a corresponding, advantageous manner. The main advantages of the process of the invention reside in the minimum total energy turnover and the particularly careful treatment of the very reactive unsaturated carboxylic acids, as a result of which the occurrence of uncontrolled reactions is minimized.

EXAMPLE

In a process for the gas-phase catalyzed oxidative preparation of acrylic acid from propylene, in which $N_2$ was used as diluent, there was obtained a reaction gas mixture having a temperature of 277° C. and exhibiting the following composition:

13.50 wt % of acrylic acid, 0.25 wt % of by-products which boil under standard pressure conditions at a temperature higher than does acrylic acid (high-boilers), 5.35 wt % of by-products which boil under standard pressure conditions at a lower temperature than does acrylic acid (low-boilers, eg $H_2O$, acrolein, formaldehyde, acetaldehyde and particularly acetic acid), 80.90 wt % of residual gas (substantially $N_2$, traces of carbon oxides and propylene).

At a rate of 220.2 kg/h, this reaction gas mixture was indirectly cooled in a shell-and-tube heat exchanger to a temperature of 204° C. The coolant used was a mixture comprising 75 wt % of diphenylether and 25 wt % of diphenyl.

The cooled reaction gas mixture was subsequently passed into a packed column (internal diameter: 316 mm) having high-grade steel walls (wall thickness: 4 mm) and containing regular Mellapak packs sold by Sulzer AG, Winterthur, Switzerland, which column was in direct contact with the ambient atmosphere (25° C.) and was designed as follows:

On a supporting grate located above the feed point for the cooled reaction gas mixture two of the aforementioned packs of type 125 Y and then sixteen of the aforementioned packs of type 250 Y (the diameter of the individual packs was 314 mm and their height was 210 mm) were directly stacked one above the other to form a first stack of packs. Below the supporting grate there was a structural unit having a length of 800 mm and designed to accept the bottoms. The feed point for the cooled reaction mixture (feed point 1) was located at the center the structural unit. 50 mm above the end of the first stack of packs there was provided a collecting plate for the descending liquid, which plate extended beyond the cross-section of the column and had a covered flue at the center to allow for the passage of the ascending steam/gas mixture (height: 400 mm; diameter: 106 mm), around which four overflow tubes (height: 300 mm; diameter: 43 mm) were mounted symmetrically.

From this collecting plate (point of withdrawal 1) there were continuously withdrawn 1700 kg/h of the liquid phase accumulating on this collecting plate and having a temperature of 59.9° C., which liquid phase was cooled to 42° C. and directly recycled at this temperature to the packed column above the end of the second stack of packs.

The second stack of packs consisted of three regular packs of the same sort (type 250 Y) and directly stacked one above the other on a supporting grate situated above the transfer flue mounted on the collecting plate and separating the point of withdrawal 1 from the recycle point. Above the recycle point there were installed 13 further packs of type 250 C. stacked one above the other (third stack of packs). At the end of this third stack of packs there was located the feed point for the absorbent (feed point 2). The absorbent used was a mixture of 57.4 wt % of diphenylether, 20.7 wt % of diphenyl, and 20 wt % of o-dimethyl phthalate. It was introduced at the feed point 2 at a temperature of 52° C. and at a rate of 160.8 kg/h.

Directly above the feed point 2 there was a dividing flue unit, above which there were stacked five further regular packs of the same sort (type 250 Y) (fourth stack of packs). Directly above the end of the fourth stack of packs there was the feed point for the circulated cold water (feed point 3). 370 kg/h of aqueous phase were withdrawn from the collecting plate of the dividing flue unit (point of withdrawal 2) and 6.7 kg/h thereof were separated and removed. The residual amount was recycled to feed point 3. Its temperature of withdrawal was 40.5° C. and it was cooled to 25° C. prior to recycling. The withdrawn aqueous phase contained 6.9 wt % of acrylic acid (loss) and 93.1 wt % of water containing low-boilers. The top of the packed column was open. 181.8 g of gaseous compounds having a temperature of 26.6° C. were given off through this opening. This off-gas consisted of 2 wt % of steam, >97.8 wt % of residual gas, <0.1 wt % of acrylic acid and<0.1 wt % of absorbent. The pressure at the top of the column was 1.15 bar, at feed point 1 1.24 bar. The organic phase accumulating at the point of withdrawal 2 was recycled to the enrichment column at feed point 2.

The withdrawal of the bottoms was effected at a rate of 192.5 kg/h, the temperature of the withdrawn bottoms being 118.4° C. The composition of the bottoms was as follows: 15.2 wt % of acrylic acid, 84.35 wt % of absorbent, 0.29 wt % of components (maleic anhydride, phthalic anhydride etc) boiling at a temperature higher than the boiling point of acrylic acid, and 0.16 wt % of low-boilers including $H_2O$.

The withdrawn bottoms were passed to a conventional rectifying column containing a regular pack (packed column containing regular packs) and were fractionally separated in known manner under reduced pressure. Acrylic acid was is isolated during this phase through a side flue in a purity>99.7 wt %. At the top of the column there occurred small amounts of low-boilers and the bottoms were reused as absorbent. Phenothiazine used for the inhibition of polymerization was similarly introduced at the top of this rectifying column.

We claim:

1. A process for the separation of (meth)acrylic acid from a reaction gas mixture formed by catalytic gas phase oxidation, by countercurrent absorption using a high-boiling inert, hydrophobic organic liquid, in which the reaction gas mixture is passed through an absorption column countercurrently to the descending high-boiling, inert, hydrophobic organic liquid and (meth)acrylic acid is subsequently fractionally separated from the liquid effluent leaving the absorption column and containing (meth)acrylic acid, wherein a rectifying process is superimposed on the absorption process occurring naturally in the absorption column by withdrawing a portion of the descending liquid phase at a point along the absorption column, cooling said withdrawn portion and subsequently recycling the cooled fluid to the absorption column at a point along the absorption column between the point of withdrawal and the feed point of the high-boiling hydrophobic absorbent.

2. The process as claimed in claim 1, wherein the withdrawal of the descending liquid phase is conducted at a point near the halfway mark of the absorption column and the liquid phase is recycled to the absorption column at a point slightly above the point of withdrawal.

3. The process as claimed in claim 1, wherein the bottom theoretical separating stage has a temperature of from 110° C. to 125° C. and the temperature at the top theoretical separating stage is 5° to 15° C. above the input temperature of the absorbent.

4. The process as claimed in claim 1, wherein the high-boiling, inert, hydrophobic organic liquid is a mixture of 70 to 75 wt. % of diphenylether and 25 to 30 wt. % of diphenyl.

5. The process as claimed in claim 1, wherein the high-boiling, inert, hydrophobic organic liquid is a mixture comprising a blend of 70 to 75 wt. % of diphenylether and 25 to 30 wt. % of diphenyl, and, based on this mixture, 0.1 to 25 wt. % of O-dimethylphthalate.

6. The process as claimed in claim 1, wherein said absorption column is a valve tray column, a bubble-cap tray column, a column filled with a loose, irregular, packing or a column filled with compact packs.

7. The process as claimed in claim 1, wherein the absorption column contains 5 to 20 theoretical separating stages.

8. The process as claimed in claim 1, wherein the reaction gas mixture entering the absorption column has a temperature of from 190° to 230° C.

9. The process of claim 8, wherein said temperature ranges from 200° to 210° C.

10. The process as claimed in claim 1, wherein the liquid absorbent entering the top of the absorption column has a temperature of from 50° to 100° C.

11. The process of claim 10, wherein said temperature ranges from 50° to 70° C.

* * * * *